(12) United States Patent
Lee et al.

(10) Patent No.: US 6,746,397 B2
(45) Date of Patent: Jun. 8, 2004

(54) METHOD FOR MEASURING HUMAN BODY AURA AND SYSTEM THEREFOR

(75) Inventors: Seung-Heun Lee, Chungbuk (KR);
Eul-Soon Lee, Seoul (KR);
Seung-Chan Ahn, Kyungbuk (KR)

(73) Assignee: BR System Co., Ltd. (KR)

( * ) Notice: Subject to any disclaimer, the term of this patent is extended or adjusted under 35 U.S.C. 154(b) by 320 days.

(21) Appl. No.: 09/915,944

(22) Filed: Jul. 26, 2001

(65) Prior Publication Data

US 2003/0023145 A1 Jan. 30, 2003

(51) Int. Cl.[7] .................... A61B 5/00; A63F 13/00; G06F 17/00; G03B 29/00; G03B 17/53
(52) U.S. Cl. .................... 600/300; 463/38; 600/549; 600/546; 600/547; 128/920; 128/898; 396/429; 396/661; 348/64
(58) Field of Search ................. 600/300–301, 600/481, 547, 546, 587, 592, 407, 549, 474; 463/36–42, 30; 396/429, 661; 348/64; 434/350–352, 336; 607/2, 50, 56; 382/128; 128/897, 898, 920, 922; 84/1, 600; 345/156, 161, 157, 173, 163; 33/1 R, 1 PT; 374/100; 702/104, 135; 704/275

(56) References Cited

U.S. PATENT DOCUMENTS 5,132,714 A * 7/1992 Samon ................... 396/429

FOREIGN PATENT DOCUMENTS

JP 410327353 A * 12/1998 .......... H04N/5/272

* cited by examiner

Primary Examiner—Max F. Hindenburg
Assistant Examiner—Michael Astorino
(74) Attorney, Agent, or Firm—Woodcock Washburn LLP

(57) ABSTRACT

A method of measuring the aura of a human body is provided wherein the method comprises putting a system for measuring aura of a human body to an initial status by first selecting from a program a mode of operating said system, wherein the mode comprises a camera-using mode and a camera non-using mode. The system is capable of measuring physiological signals of a human body. According to the method, a timer function is selected on the system to use a timer through a program that delays the reading of the physiological signals of the person tested for about 5–10 seconds, two palms are contacted on aura sensing part for measuring physiological signals of a human body, the physiological signals of the human body are read from the sensors with the system, and the aura image of the physiological signals is displayed on a monitor.

5 Claims, 7 Drawing Sheets

METHOD FOR MEASURING HUMAN BODY AURA AND SYSTEM THEREFOR

FIELD OF THE INVENTION

The present invention relates to a system for measuring human body aura. More specifically, the present invention relates to a system for measuring human body aura, in which physiological signals of palms, foot soles and fingers due to temperature, blood flow, heart pulse, electrodermatography, electromyography and the like can be sensed, and the sensed data can be analyzed by a computer, so that the internal energy state of a person as a test object can be displayed in a monitor or an LCD panel, thereby making it possible to visually confirm the symptom of the person. Further, the present invention relates to a method for measuring a human body aura.

BACKGROUND OF THE INVENTION

Recently, the oriental conception "Gi" (power state) is frequently talked in everyday life. The words related to the power state are numerous including "the feeling is good", "the feeling is absolutely obstructed", "the spirit is down", "high spirited", "exhausted", "absolutely exhausted", "dominatingly spirited", "popular and esteemed", and the like.

This is a power state or an energy state. The power state has no size, shape, weight or odor, but it is the motive force for moving the human body. The power state is transmitted in the form of sound, light and other waves.

The power state of human body can be classified into motive power, general power, and true power. The motive power is that which has been innately gifted, and the general power is based on the energy which is obtained from the oxidation of the ingested food to use it in everyday life.

The true power can be obtained through the concentration of spirit. That is, it can be obtained through a long term training. The true power can be adjusted by mind, and the power state of this kind is varied depending on the state of mind.

In 1939, Kirlian who was a Russian electrician showed a power state photograph through a machine which had been invented by him. The photograph was presented to an audience which consisted of eminent scientists. The photograph showed the bio-energy which was radiated from the human body, and this is called "Kirlian photograph".

A scientist brought two leaves of a plant to Kirlian, and asked him to photograph them. When the leaves were photographed, the result was that one of them showed a clear and definite color, and the other showed only a fading color.

The reason was that the latter leaf was that which was infected to an illness. In this occasion, Kirlian said that a biological entity has two aspects, and one of them is the visible physical body, while the other is an energy entity (a second body) which can be confirmed only by a photograph.

This theory can be applied also to the human body. If this can be applied to the medical science, then a drastic result can be obtained, because then any illness can be diagnosed in advance.

This is meant that if the power state of the human body can be confirmed visually, then it will become a medically useful means.

Kendal Johnson of the United States carried out a research on the Kirlian photograph. He elucidated the following facts. That is, a definite aura can be observed in a human body which has been loosened by meditation.

Further, if a critical point of human body is stimulated, then the aura radiation is increased around the fingers. Further, a patient who received a power state treatment showed a more definite brighter aura than he who has not been treated.

The resonance magnetic analyzer which is being developed currently in the United States can diagnose the disordered part of the internal organs by detecting the waves which are radiated from the relevant organ.

The U.S. physician Dr. Albert Abrahms found that not only the different organs of human body radiate different kinds of waves, but also the radiations from bacteria of various illness are of different kinds.

As described above, the power state which is the spiritual and physical status of the human body can be expressed by visual means such as color and shape.

When a person as a test object mounts his or her palm on a sensor, the physiological signals or thermal energy emanating therefrom are not always same.

If the feeling of the tested person is not good, or if there is an abnormality such as stress, then the measured result will be different from the normal person.

If one of parents or other close relatives has died, or if the business has been failed, or if there is an excessive exhaustion, then the variation of the internal energy will be great.

If this internal energy state can be measured and visually confirmed, then this means will be widely used to protect his or her own health.

The photo-sensing polaroid camera is the conventional means which can measure the internal energy state of human body to provide a visually confirmable data.

That is, a person as a test object is photographed, and color and shape are formed to show the internal status of the test object.

However, the conventional polaroid camera is inconvenient to handle it by a single person, the result cannot be obtained immediately, and the analysis cannot be carried out without being helped by a professional person.

In order to overcome the above described disadvantages of the conventional technique, the present inventors have invented a system in which the manipulation is easy, and the analysis of the result can be carried out even without an assistance of a professional person.

SUMMARY OF THE INVENTION

It is an object of the present invention to provide a system by which one's own internal energy state can be measured.

It is another object of the present invention to provide a system in which the measured internal energy state can be confirmed by a computer monitor or an LCD panel on a real time basis.

It is still another object of the present invention to provide a system in which a person as a test object can analyze the image of his or her own internal energy state even without a help of a professional person.

It is still another object of the present invention to provide a system in which human body aura can be made formed on the figure of the measured person at the measured time.

All the above objects and other objects can be accomplished by the detailed descriptions presented below.

The system for measuring aura of a human body according to the present invention includes: an aura sensing part 1 to be contacted to a human body, for measuring the physiological signals of the human body; and a data processing system 2 for processing the aura data of the physiological signals.

Further, the aura sensing part according to the present invention includes a left hand measuring sensor 100 and a right hand measuring sensor 200, to be contacted to the palms of the human body.

The left hand measuring sensor 100 according to the present invention includes: a thumb sensor 105, a first finger sensor 104, a second finger sensor 103, a third finger sensor 102, a fourth finger sensor 101, an upper palm sensor 106, an intermediate palm sensor 107 and a lower palm sensor 108, for measuring the physiological signals radiating from the fingers and palm.

The right hand measuring sensor 200 according to the present invention includes: a thumb sensor 201, a first finger sensor 202, a second finger sensor 203, a third finger sensor 204, a fourth finger sensor 205, an upper palm sensor 206, an intermediate palm sensor 207 and a lower palm sensor 208, for measuring the physiological signals radiating from the fingers and palm.

The data processing system 2 according to the present invention includes: a computer 21 for processing the obtained data; a monitor 22 and/or a printer 23 for outputting the processed data; and a camera 24 for photographing the person as a test object.

BRIEF DESCRIPTION OF THE DRAWINGS

The above objects and other advantages of the present invention will become more apparent by describing in detail the preferred embodiments of the present invention with reference to the attached drawings, in which.

DETAILED DESCRIPTION OF THE PREFERRED EMBODIMENTS

Figure 1:
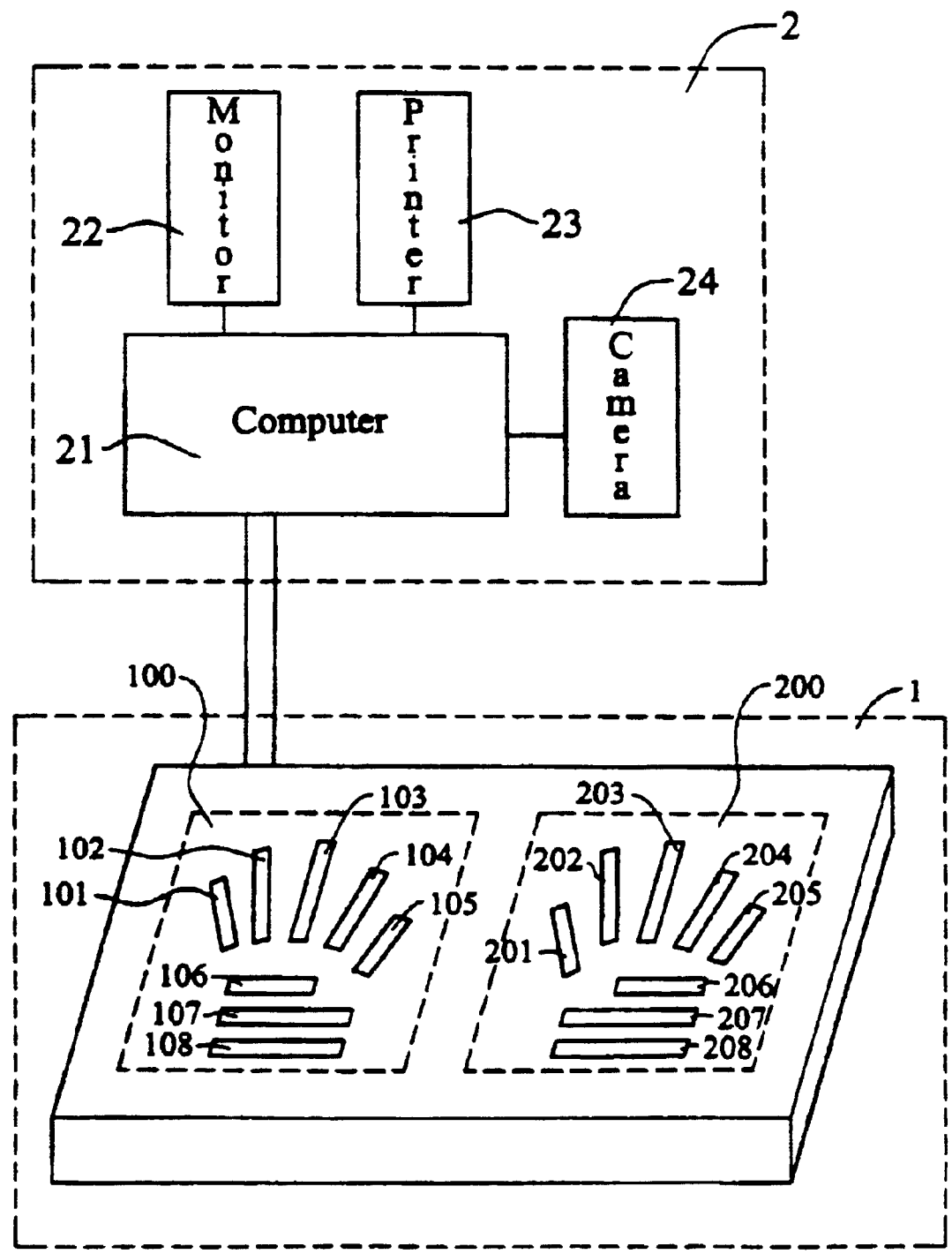
FIG. 1 is a block diagram showing the constitution of the palm-contacting type human body aura measuring system according to the present invention.

The preferred embodiments of the present invention will be described in detail referring to the attached drawings.

The system for measuring the aura of the human body according to the present invention includes: an aura sensing part 1 to be contacted to a human body, for measuring the physiological signals of the human body; and a data processing system 2 for processing the aura data of the physiological signals. Further, the aura sensing part according to the present invention includes a left hand measuring sensor 100 and a right hand measuring sensor 200, to be contacted to the palms of the human body. The left hand measuring sensor 100 according to the present invention includes: a thumb sensor 105, a first finger sensor 104, a second finger sensor 103, a third finger sensor 102, a fourth finger sensor 101, an upper palm sensor 106, an intermediate palm sensor 107 and a lower palm sensor 108, for measuring the physiological signals radiating from the fingers and palm. The right hand measuring sensor 200 according to the present invention includes: a thumb sensor 201, a first finger sensor 202, a second finger sensor 203, a third finger sensor 204, a fourth finger sensor 205, an upper palm sensor 206, an intermediate palm sensor 207 and a lower palm sensor 208, for measuring the physiological signals radiating from the fingers and palm.

The data processing system 2 according to the present invention includes: a computer 21 for processing the obtained data; a monitor 22 and/or a printer 23 for outputting the processed data; and a camera 24 for photographing the person as a test object.

FIG. 1 is a block diagram showing the constitution of the palm-contacting type human body aura measuring system according to the present invention.

The system for measuring the aura of the human body according to the present invention includes: an aura sensing part 1 to be contacted to a human body, for measuring the physiological signals of the human body; and a data processing system 2 for processing the aura data of the physiological signals.

Further, the aura sensing part according to the present invention includes a left hand measuring sensor 100 and a right hand measuring sensor 200, to be contacted to the palms of the human body.

The left hand measuring sensor 100 according to the present invention includes: a thumb sensor 105, a first finger sensor 104, a second finger sensor 103, a third finger sensor 102, a fourth finger sensor 101, an upper palm sensor 106, an intermediate palm sensor 107 and a lower palm sensor 108, for measuring the physiological signals radiating from the fingers and palm.

That is, the physiological signals of human hands due to temperature, blood flow, heart pulse, electrodermatography, electromyography and the like are accurately measured.

The right hand measuring sensor 200 according to the present invention includes: a thumb sensor 201, a first finger sensor 202, a second finger sensor 203, a third finger sensor 204, a fourth finger sensor 205, an upper palm sensor 206, an intermediate palm sensor 207 and a lower palm sensor 208, for measuring the physiological signals radiating from the fingers and palm. That is, the physiological signals of human hands due to temperature, blood flow, heart pulse, electrodermatography, electromyography and the like are accurately measured.

The data processing system 2 analyzes the physiological signals of the human palms obtained from the temperature, blood flow, heart pulse, electrodermatography, electromyography and the like. The result is outputted to a monitor 22 or a printer 23, and in order to increase the reality sensation of the outputted image, the person as a test object is actually captured.

The data processing system 2 according to the present invention includes: a computer 21 for carrying out the overall control; a monitor 22 and/or a printer 23 for outputting the processed data; and a camera 24 for capturing the person as a test object.

Figure 2:
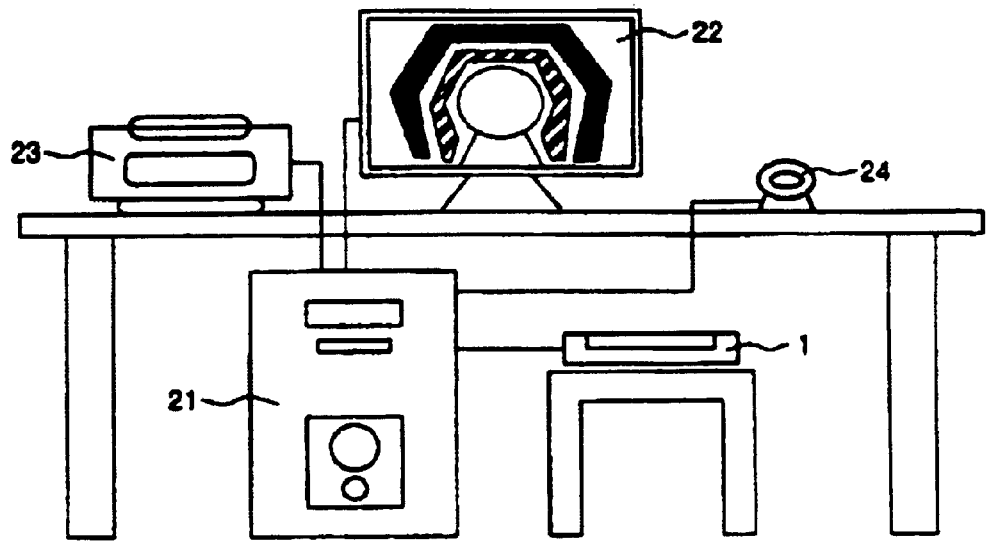
FIG. 2 is a frontal view showing the constitution of the palm-contacting type human body aura measuring system according to the present invention.
Figure 3:
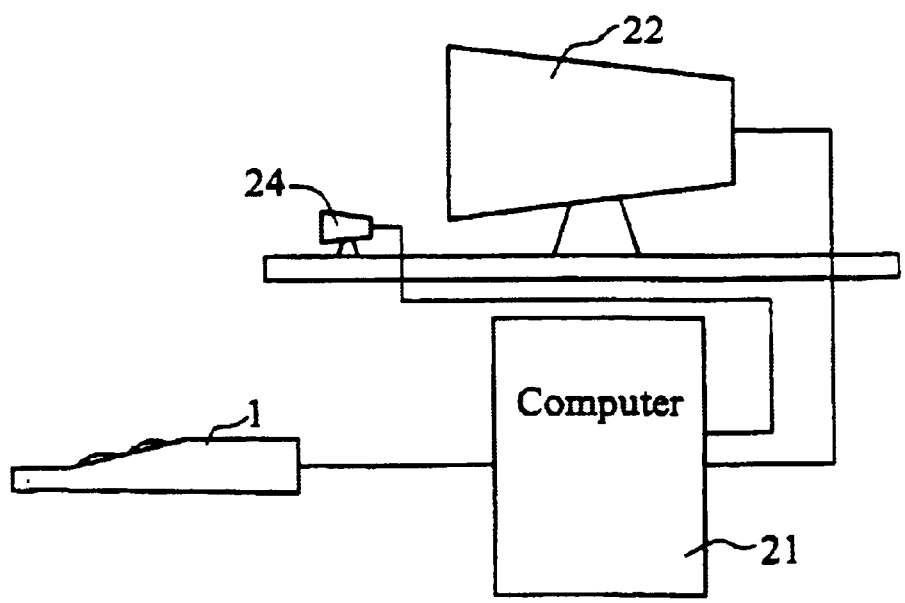
FIG. 3 is a side view showing the constitution of the palm-contacting type human body aura measuring system according to the present invention.

FIG. 2 is a frontal view showing the constitution of the palm-contacting type human body aura measuring system according to the present invention. FIG. 3 is a side view showing the constitution of the palm-contacting type human body aura measuring system according to the present invention.

The reason why the human palm is contacted in measuring the human body aura is that the human palm is very sensitive compared with the other portions of the human body, and the emanation of aura is intensive.

Figure 4:
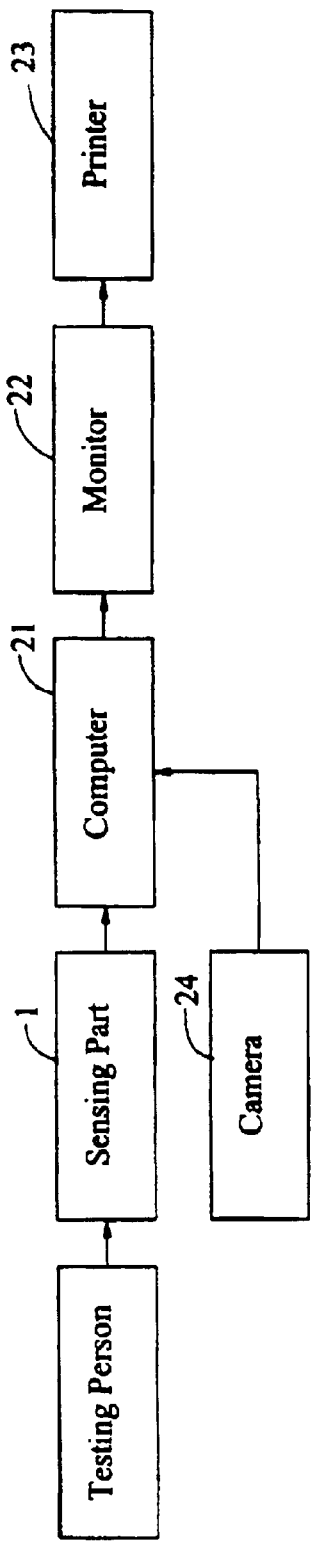
FIG. 4 is a flow chart showing the constitution of the palm-contacting type human body aura measuring system according to the present invention.
Figure 5:
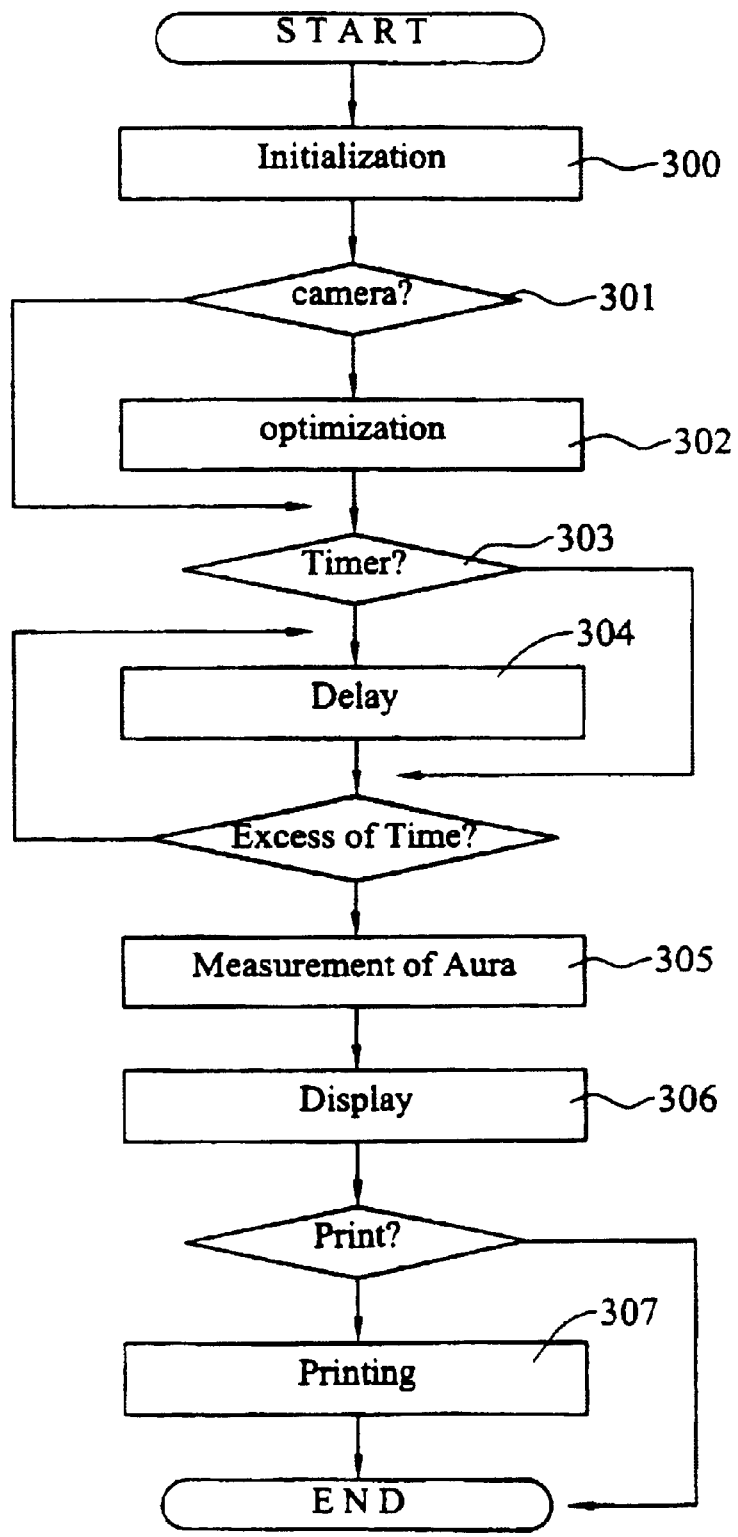
FIG. 5 is a flow chart showing the constitution of the measuring procedure for the palm-contacting type human body aura measuring system according to the present invention.

FIG. 4 is a flow chart showing the constitution of the palm-contacting type human body aura measuring system according to the present invention. FIG. 5 is a flow chart showing the constitution of the measuring procedure for the palm-contacting type human body aura measuring system according to the present invention.

The aura measuring method in which the palm is contacted is carried out in the following manner. That is, at first the person as a test object drives the computer, and selects one of the modes among a camera using mode and a camera non-using mode.

The camera-using mode is for capturing the real entity image of the test object after measuring the aura, so that a real sensation of the image can be obtained.

In the case where the camera-using mode is selected, the measuring method is carried out in the following manner. That is, the person as a test object selects the camera-using mode, and makes his or her own figure displayed on the screen.

That is, the image of the human body which is displayed on the monitor 22 has been properly adjusted, but an additional adjustment is carried out suitably to a certain standard size of the image.

If the captured image appears on the monitor 22, then the person as a test object selects the timer function which has been provided in the program menu.

If the person as a test object is in a passive situation, and if a separate operator helps the measurement, then the timer function is not required.

However, if the person as a test object carries out the measurement for himself or herself without any assistance of an operator, then the selection of the timer function has to be necessarily carried out.

The reason is as follows. That is, the person as a test object cannot simultaneously contact his or her hands to the sensors 100 and 200 while manipulating the computer. If the timer function is not employed, then the aura measurement can be carried out only with an assistance of an operator.

The timer function delays the measurement of the physiological signals for a time period of about 5–10 second during which the execution button is pressed and the two hands are moved to the sensors 100 and 200.

The set time of the timer is not necessarily limited to the above mentioned period, but can be easily varied by those ordinarily skilled in the art.

If the set time of the timer elapses, then the computer reads the physiological signals from the hands which have been placed on the sensors 100 and 200. The data thus read is processed by the computer, and the processed results are displayed on the monitor 22 on a real time basis.

The image which has been displayed can be outputted to a printer 23, and a detailed interpretation can be made to be accompanied to the printed image, so that the person as a test object can easily understand the analyzed aura.

Referring to FIG. 5, the procedure of the operation will be described in detail. First, the person as a test object decides as to whether the camera will be used or not. If the use of the camera is selected, then the relevant computer program is executed to optimize the image of the person as a test object.

When the image optimization step is completed, the person as a test object decides as to whether the timer function will be selected or not through the computer program. If the measurement is carried out for oneself, this step has to be necessarily carried out.

If the person has selected the use of the timer function, the computer delays the reading of the human physiological signals from the sensors for a period of time (about 5–10 seconds) through the relevant program.

Then the timer is driven by manipulating the computer, and then, an operating button is clicked so that the computer would read the physiological signals of the person from the sensors 100 and 200. Then the two hands are placed on the aura sensing part.

When the set period of the timer elapses, the computer begins to read the physiological signals of the person, and then, analyzes the physiological signals. Then the analyzed results are displayed on the monitor to show the aura of the person on a real time basis.

The outputted aura image of the monitor can not only be stored in a form of a file, but also can be outputted to a printer together with an interpretation on it.

The interpretation of the aura image is stored as a data base in the form of color and shape. In accordance with the color and shape of the aura, diversified interpretations are provided.

FIG. 5 is a flow chart showing the constitution of the measuring procedure for the palm-contacting type human body aura measuring system according to the present invention. In this procedure, first the relevant program of the computer is driven, and the computer is put to an initial status (step 300).

Whether a camera is to be used or not is decided by using the program (step 301), and if the camera is to be used, the image of the person as a test object is optimized (step 302). If it has been decided that the camera is not to be used, then this step is skipped.

The person as a test object decides through the program as to whether the timer function is to be used or not (step 303). If the timer function has been selected, then the reading of the physiological signals of the person is delayed for a certain period of time, for instance, about 5□10 seconds (step 304).

If an operator is present to assist the measurement, this step is skipped.

If the set time of the timer elapses, then the system starts to read the physiological signals of the human body from the sensors (step 305).

After reading the physiological signals of the human body from the sensors, the aura image of the person is outputted to the monitor (step 306). In accordance with the selection by the person as a test object, the aura image data is stored in a form of a file, or is printed out together with an interpretation of the aura (step 307).

Figure 6:
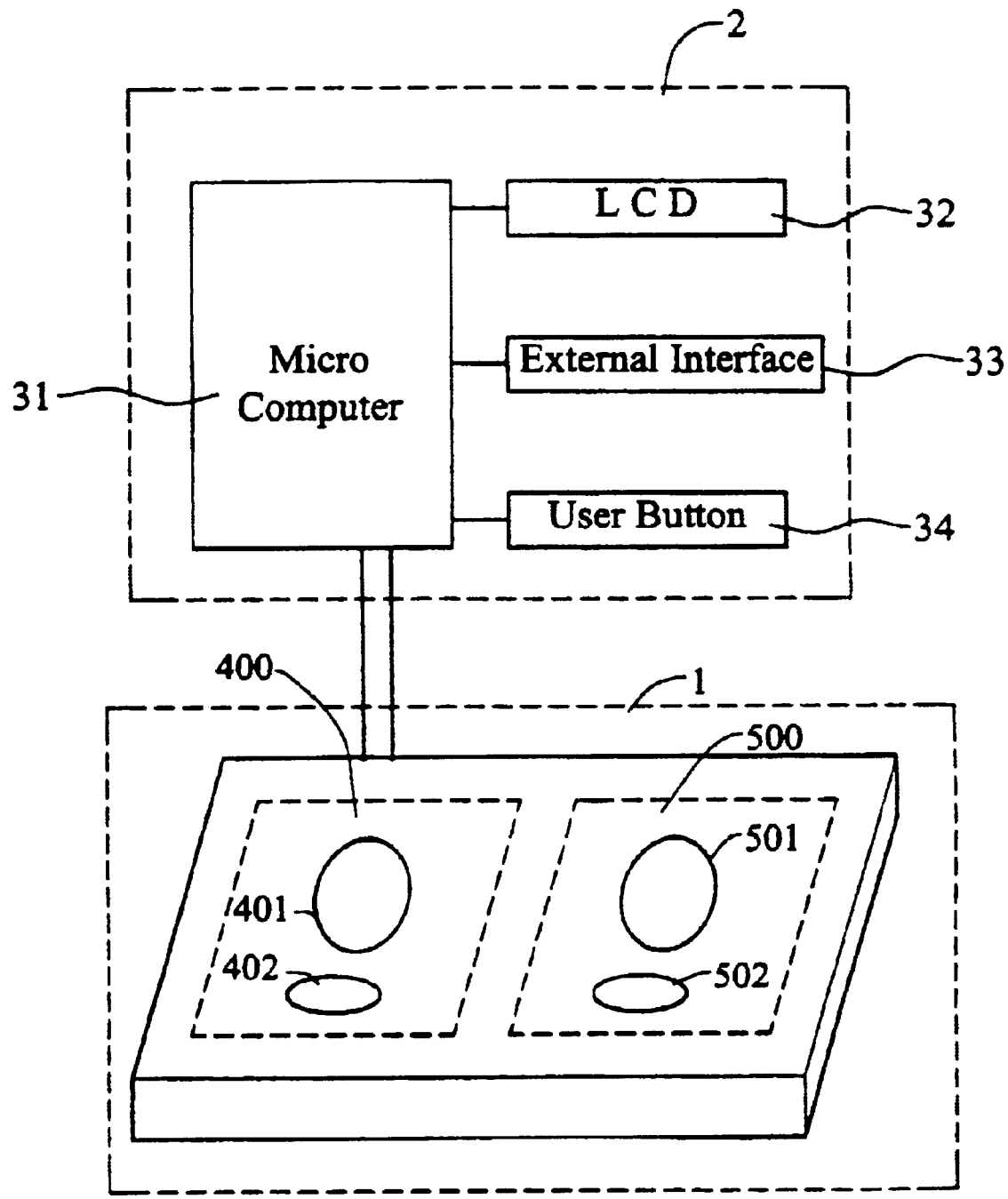
FIG. 6 is a block diagram showing the constitution of the foot sole-contacting type human body aura measuring system in another embodiment of the present invention.

FIG. 6 is a block diagram showing the constitution of the foot sole-contacting type human body aura measuring system in another embodiment of the present invention.

The two-foot-sole-contacting type human body aura measuring system according to the present invention includes: an aura sensing part 1 for sensing the physiological signals by being contacted to two foot soles; and a data processing system 2 for processing the sensed physiological signals.

The aura sensor part according to the present invention includes: a left foot sole measuring sensor 400; and a right foot sole measuring sensor 500. The right foot sole measuring sensor according to the present invention includes: a front foot sole sensor 501 and a rear foot sole sensor 502. The left foot sole measuring sensor according to the present invention includes: a front foot sole sensor 401 and a rear foot sole sensor 402.

The data processing system includes: a microcomputer 31 for processing the measured data; an LCD 32 for outputting the processed data; an external interface 33 for transmitting the measured data to an external apparatus or for receiving an analyzed data from an external apparatus; and a user button 34 for manipulating the computer system to watch the aura data expression results.

The foot sole-contacting type aura measuring system can be built in connection with a body weight scale.

In this case, the person can stand upon the sensor part, and manipulate the user buttons to measure the aura. Thus the measured aura can be read through the scale window.

Figure 7:
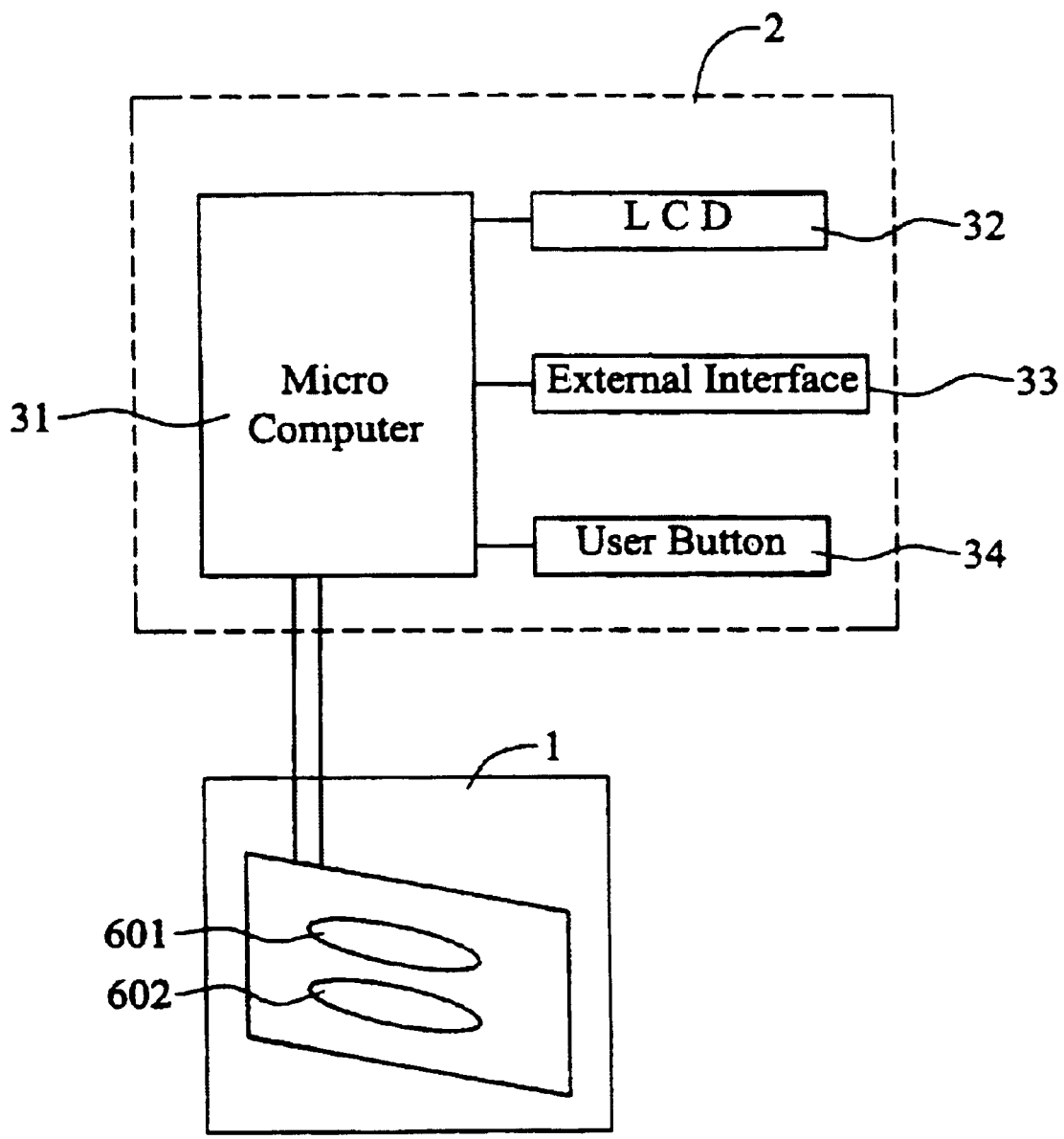
FIG. 7 is a block diagram showing the constitution of the two-finger-contacting type human body aura measuring system in still another embodiment of the present invention.

FIG. 7 is a block diagram showing the constitution of the two-finger-contacting type human body aura measuring system in still another embodiment of the present invention.

The two-finger-contacting type human body aura measuring system in still another embodiment of the present invention includes: an aura sensing part 1 for sensing the physiological signals by being contacted to two fingers; and a data processing system 2 for processing the measured data.

The aura sensing part according to the present invention includes: a left finger sensor 601 and a right finger sensor 602.

The data processing system includes: a microcomputer 31 for processing the measured data; an LCD 32 for outputting the processed data; an external interface 33 for transmitting the measured data to an external apparatus or for receiving an analyzed data from an external apparatus; and a user button 34 for manipulating the computer system to watch the aura data expression results.

The two-finger-contacting type human body aura measuring system of FIG. 7 in still another embodiment of the present invention can be applied to a mobile phone. In this case, the two sensors 601 and 602 can be installed on the cover or main body of the mobile phone, and the measured results can be read through the LCD window or a computer.

Further, through the mobile phone, the measured aura can be transmitted to a relevant server, and an interpretation on the measured aura can be received from the server.

Figure 8:
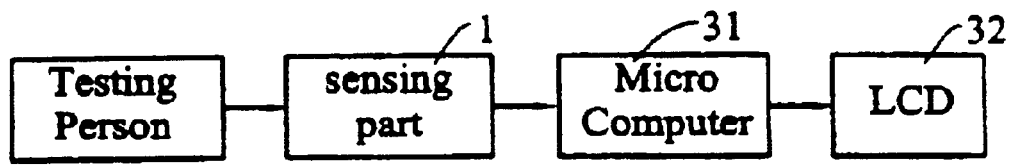
FIG. 8 is a flow chart showing the constitution of the foot sole-contacting type or two-finger-contacting type human body aura measuring system according to the present invention.
Figure 9:
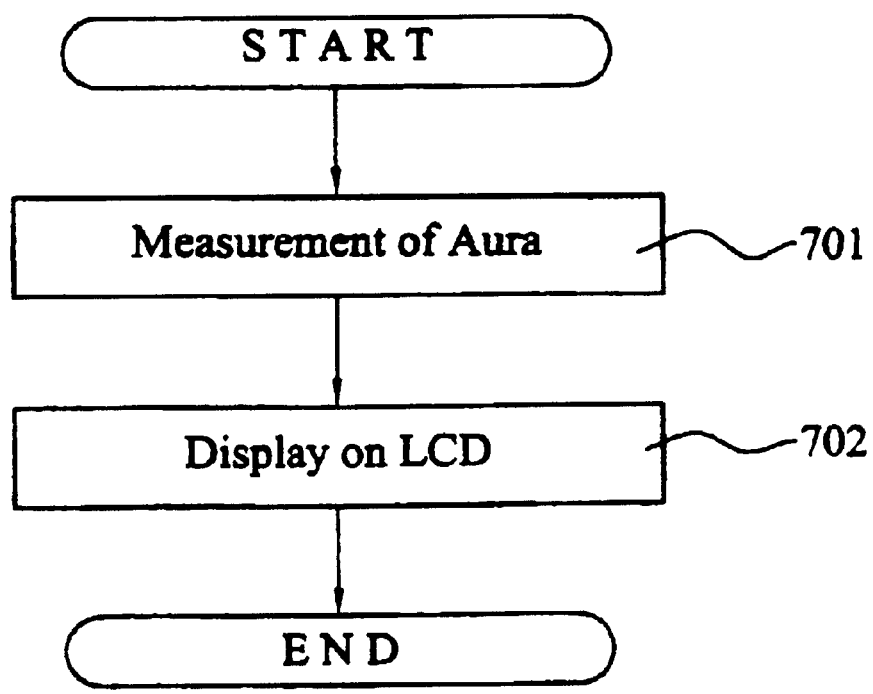
FIG. 9 is a flow chart showing the constitution of the measuring procedure for the foot sole-contacting type or two-finger-contacting type human body aura measuring system according to the present invention.

FIG. 8 is a flow chart showing the constitution of the foot sole-contacting type or two-finger-contacting type human body aura measuring system according to the present invention. FIG. 9 is a flow chart showing the constitution of the measuring procedure for the foot sole-contacting type or two-finger-contacting type human body aura measuring system according to the present invention.

Referring to FIG. 8, the operating procedure will be described in detail below. First, two fingers are contacted to the respective sensors.

Then the physiological signals of the human body are read by manipulating the user button 34. After a moment, the physiological signals which have been read and processed by the microcomputer 31 are outputted to the LCD 32 on a real time basis.

The aura images which are outputted to the LCD can also be outputted through the external interface 33 to an external printer to be printed on a paper.

Referring to FIG. 9, the operating procedure of the present invention will be described in detail below. In the two-foot-sole-contacting type aura measuring system, the measuring person can use his or her two hands during the measurement, and therefore, a time delay is not required.

Accordingly, if the measuring person starts the measurement by manipulating the user button 34, then the physiological signals of the human body are measured (step 701), and the measured aura is outputted to the LCD (step 702).

Specifically, in this embodiment, the present invention includes a data processing system and an aura sensing part.

Although it is not illustrated in the drawing, a program which is capable of executing the present invention is installed in the memory of the computer.

The camera, the interface, the user buttons and the printer are the optional elements, and therefore, they can be properly selected in accordance with the needs.

According to the present invention as described above, the system can be easily utilized to measure the internal energy state for oneself, and the measured energy state can be confirmed on a real time basis through a computer monitor or through an LCD.

Further, the image of the internal energy state can be analyzed for oneself without being assisted by a professional person, and the reality sensation of the measured aura image can be improved.

In the above, the present invention was described based on the specific preferred embodiments and the attached drawings, but it should be apparent to those ordinarily skilled in the art that various changes and modifications can be added without departing from the spirit and scope of the present invention which will be defined in the appended claims.

What is claimed is:

1. A method of measuring aura of a human body comprising:
    a) initializing a system for measuring aura of a human body by first selecting a mode of operating said system, wherein said mode comprises a camera-using mode and a camera non-using mode, said system is capable of measuring data in the form of physiological signals of a human body;
    b) selecting a timer function on said system to use a timer through a program and delaying reading of the physiological signals of the person tested for about 5–10 seconds;
    c) contacting two palms on an aura sensing part for measuring physiological signals of a human body;
    d) collecting the physiological signals data of the human body from the sensors with the system; and
    e) displaying an aura image of the physiological signals on a monitor.

2. The method of claim 1 wherein said system for measuring aura comprises:
    an aura sensing part adapted to be contacted to two palms, for measuring the physiological signals of the human body; and
    a data processing system for processing the physiological signals data, wherein the data processing system include a computer for processing the obtained data;

a monitor and/or a printer for outputting the processed data; and a camera for photographing a person as a test object.

3. The method of claim 2 wherein said aura sensing part comprises a left hand measuring sensor and a right hand measuring sensor adapted to be contacted to the palms of the human body, wherein the left hand measuring sensor includes a thumb sensor, a first finger sensor, a second finger sensor, a third finger sensor, a fourth finger sensor, an upper palm sensor, an intermediate palm sensor and a lower palm sensor, for measuring the physiological signals radiating from the fingers and palm, and the right hand measuring sensor includes a thumb sensor, a first finger sensor, a second finger sensor, a third finger sensor, a fourth finger sensor, an upper palm sensor, an intermediate palm sensor and a lower palm sensor, for measuring the physiological signals radiating from the fingers and palm.

4. The method of claim 1 wherein said system for measuring aura comprises:

an aura sensing part adapted to be contacted to two feet soles, for measuring the physiological signals of the human body; and a data processing system for processing the physiological signal data, wherein the data processing system includes microcomputer for processing the measured data;

an LCD for outputting the processed data;

an external interface for transmitting the measured data to an external apparatus or for receiving an analyzed data from an external apparatus; and a user button for manipulating the computer system.

5. The method of claim 1 said system for measuring aura comprises:

an aura sensing part adapted to be contacted to two fingers, for measuring the physiological signals of the human body; and a data processing system for processing the physiological signal data, wherein the aura sensing part includes a left finger sensor and a right finger sensor, and the data processing system includes a microcomputer or processing the measured data;

an LCD for outputting the processed data;

an external interface for transmitting the measured data to an external apparatus or for receiving an analyzed data from an external apparatus; and a user button for manipulating the computer system.

* * * * *

UNITED STATES PATENT AND TRADEMARK OFFICE
CERTIFICATE OF CORRECTION

PATENT NO. : 6,746,397 B2
DATED : June 8, 2004
INVENTOR(S) : Seung-Heun Lee, Eul-Soon Lee and Seung-Chan Ahn It is certified that error appears in the above-identified patent and that said Letters Patent is hereby corrected as shown below:

<u>Column 10,</u>
Line 16, "or" should read -- for --

Signed and Sealed this

Fourteenth Day of September, 2004

JON W. DUDAS
*Director of the United States Patent and Trademark Office*